United States Patent [19]

Catherall

[11] 4,048,846

[45] Sept. 20, 1977

[54] PRESSURE RESPONSIVE APPARATUS

[75] Inventor: Reginald Catherall, Woking, England

[73] Assignee: Bell & Howell Limited, Basingstoke, England

[21] Appl. No.: 688,428

[22] Filed: May 20, 1976

[30] Foreign Application Priority Data

May 30, 1975 United Kingdom ............... 23719/75

[51] Int. Cl.² ............................................. G01N 29/02
[52] U.S. Cl. .................................... 73/67.2; 73/398 R
[58] Field of Search ................ 73/32 A, 67.2, 67.5 R, 73/71.5 R, 53, 54, 398 R, 37

[56] References Cited

U.S. PATENT DOCUMENTS

| | | | |
|---|---|---|---|
| 2,518,348 | 8/1950 | Mason | 73/54 |
| 3,021,711 | 2/1962 | Arvidson | 73/32 A X |
| 3,411,344 | 11/1968 | Lloyd | 73/67.2 |
| 3,585,843 | 6/1971 | Stansfeld | 73/71.5 R X |
| 3,626,749 | 12/1971 | Abbotts | 73/67.2 X |
| 3,911,726 | 10/1975 | Georgiev | 73/67.5 R X |

*Primary Examiner*—Richard C. Queisser
*Assistant Examiner*—Joseph W. Roskos
*Attorney, Agent, or Firm*—Richard L. Myers

[57] ABSTRACT

Apparatus responsive to the pressure of a fluid contained in or surrounding a stiff but resilient hollow body comprises a stiff, but resilient ring mounted concentric with the body by means of four equi-spaced radially extending stiff struts. Electromagnetic means is provided for exciting natural vibrations of the ring at a resonance frequency, which will be dependent upon the pressure of the fluid in the body. Means is provided for measuring the frequency of vibration, enabling the pressure of the fluid to be determined, e.g. from a pressure-frequency calibration curve for the apparatus.

27 Claims, 5 Drawing Figures

PRESSURE RESPONSIVE APPARATUS

BACKGROUND OF THE INVENTION

This invention relates to apparatus responsive to the pressure or the pressure and density of a fluid.

SUMMARY OF THE INVENTION

According to the invention there is provided apparatus responsive to the pressure of a fluid contained in or surrounding a stiff but resilient hollow body, comprising a stiff but resilient ring concentric with the body and having 2n (where n is an integer greater than 1) equispaced radially extending struts connected between a periphery of the ring and a peripheral surface of the body, means for exciting natural vibrations of the ring at a resonance frequency and means for providing a signal representative of the frequency of said vibrations. The frequency of said vibrations of the ring is dependent upon the pressure of a fluid in contact with the body.

Preferably the hollow body is a cylindrical member concentric with the ring.

The ring can be outside the body in which case the fluid is preferably supplied to the inside of the body.

The hollow body may be provided with 2n piston diaphragms in the wall thereof, wherein opposed diaphragms are arranged substantially parallel to each other, and an end of each strut is connected to the centre of an associated diaphragm.

The ring may be cylindrical and can be of circular cross-section but suitably it is of oblong cross section with its minor axis extending in the radial direction. Preferably it is of rectangular cross-section.

The means for exciting natural vibrations in the ring is so arranged that points of minimum radial deflection of the ring occur at the points of connection to the struts.

The means for exciting natural vibrations in the ring may be selectively arranged to cause the points of maximum radial deflection of the ring to occur at the points of connection to the struts, whereby the frequency of said vibrations is dependent upon the pressure and the density of the fluid under investigation.

The ring may comprise 2n rectilinear, stiff but resilient limbs with the struts connected to the junctions thereof. Preferably n = 2 and the ring is in the form of a square.

DESCRIPTION OF THE DRAWINGS

The invention will now be described by way of example with reference to the accompanying drawings, in which.

Figure 1:
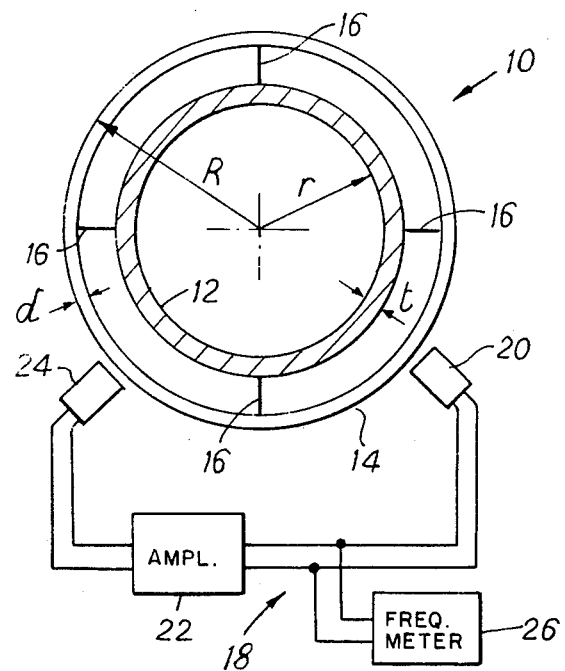
FIG. 1 is a cross-sectional view of one embodiment of apparatus according to the invention.

In the drawings the constituent parts of the apparatus are not drawn to scale.

Referring to FIG. 1 there is shown a cross-sectional view of a simple embodiment of apparatus 10 according to the invention responsive to the pressure of a fluid in a stiff, but resilient hollow body in the form of a cylindrical tube 12. The apparatus 10 comprises a stiff but resilient circular ring 14 mounted concentrically around the tube 12 by means of four, equispaced struts 16 which extend radially between the tube 12 and the ring 14. The ring 14 is of rectangular cross-section with its major axis parallel to the axis of the tube 12 so that the preferred direction of vibration of the ring is in a plane containing the minor axis. The struts 16 are so formed that they are stiff relative to the ring 14.

The tube 12, ring 14 and struts 16 are made from a ferromagnetic stainless iron/nickel/chromium alloy Ni-span C 902 (trade mark). Ni-Span C 902 is used because of its low temperature coefficient of Young's, which is dependent to some extent upon the degree of cold working it is subjected to and its subsequent heat treatment. However other materials could be used, particularly for tube 12 where the choice of material will be dependent to some extent upon the fluid it is to contain.

The tube 12 is provided with an inlet and outlet through which the fluid under investigation can pass, but the tube could, of course, be closed at one end and provided with a port at the other end whereby fluid can be charged into and discharged from the tube.

Electromagnetic drive means 18 is provided to excite the ring 14 to vibrate continuously at its natural frequency. The drive means 18 comprises a drive coil 20 driven by a maintaining amplifier 22 and an electromagnetic velocity sensor in the form of a pick-up coil 24 is arranged to provide an electrical output signal representative of the frequency of said vibrations to the input of the amplifier 22. The drive coil 20 and pick-up coil 24 are each provided with a bias magnet to prevent frequency doubling. The output of the amplifier is also connected to a frequency meter 26 for providing a visual, or other, indication of the said vibration.

The electromagnetic drive means 18 is so arranged that the ring 14 vibrates in such a manner that the struts 16 are at points of zero radial deflection (which can be likened to nodes) of the ring when the frequency of vibration of the ring is dependent upon the pressure of the fluid in the tube 12.

In operation when the tube 12 is filled with a fluid under pressure, the tube will tend to expand and this expansion will be transmitted by way of the struts 16 to the ring 14 whereby the tension in the ring 14 will be increased.

To measure pressure alone the ring 14 is arranged to vibrate in the fundamental in-phase bending mode with nodes at the struts. The frequency of vibration for this mode is equal to the zero tension frequency times an amplification factor caused by pressure.

$$f = \frac{1}{2\pi} \sqrt{\frac{36}{5} \frac{EIg_4}{\gamma AR} a^2} = f_o a$$

where
- $f_o$ = frequency with zero tension
- $a$ = amplification factor caused by pressure.
- $E$ = Young's Modulus.
- $I$ = second moment of area of ring 14 cross-section = $hd^3/12$ for rectangular cross-section ring.
- $\gamma$ = specific weight of material of ring 14 in lb/in$^3$
- $W$ = force in the struts 16 caused by pressure.
- $R$ = radius of the ring 14.
- $A$ = cross-sectional area of ring 14.
- $h$ = the dimension of the major axis of the ring cross-section.

$d$ = the dimension of the minor axis of the ring cross-section.

$$a^2 \simeq 1 + \frac{0.8}{\pi} \frac{WR^2}{EI} = 1 + kp \quad (2)$$

where $p$ is the pressure difference between the inside and outside of tube 12 and $k$ is the change of $a^2$ per unit change of $p$.

$W$ can be determined from a knowledge of the pressure and the flexibilities of the ring 14 and tube 12.

Let $f_1$ be the flexibility of the tube due to pressure of fluid
Let $f_2$ be the flexibility of the tube due to force W
Let $f_3$ be the flexibility of the ring due to forces W Then the radial expansion of ring 14 = deflection of tube 12

$$Wf_3 = pf_1 = Wf_2$$

Hence $$W = \frac{f_1 p}{f_2 + f_3} \quad (3)$$

and so $$a^2 \simeq 1 + \frac{0.8}{\pi} \cdot \frac{R^2}{EI} \cdot \frac{f_1}{(f_2 + f_3)} p \text{ and } k = \frac{0.8}{\pi} \cdot \frac{R^2}{EI} \cdot \frac{f_1}{(f_2 + f_3)}$$

It can be shown that $f_3 \simeq 0.006079 \, (R^3/EI)$ and the maximum stress in ring $\sigma_R \simeq 0.81972(R/d)(W/A)$ Substituting for $\sigma_R$ into equation (2) gives $$a^2 = 1 + 3.7278 \frac{R}{d} \cdot \frac{\sigma_R}{E} \quad (4)$$

The maximum stress $\sigma_R$ and Young's modulus for a given ring material will be known. By selecting a working stress for the ring 14 based on yield stress multiplied by a safety factor and knowing the value of E it is possible to express $a^2$ as a function of the fraction $R/d$. For Ni-Span-C 902, given a safety factor of 2, yield stress of 120,000 lb/in² and Young's modulus of 28 × 10⁶lb/in²

$$a^2 \simeq 1 + 7.988 \times 10^{-3}(R/d)$$

The gearing factor of the apparatus is defined as the percentage change of pressure or density of the fluid in the tube 12 per unit percentage change of frequency.

Since $f^2 \simeq f_o^2 a^2$ from equations (2) and (3) this can be restated as:

$$f^2 \simeq f_o^2 (1 + kp)$$

and then $$\frac{df}{f} = \frac{1}{2(1 + 1/kp)} \cdot \frac{dp}{p} \text{ and}$$

Gearing factor = $2(1 + 1/kp)$

Ideally the gearing factor should be arranged to be small and for a practicable apparatus it is preferred that it should not exceed about 5. Thus in the present example $R/d$ = 83.

It can be shown that the flexibilities for the thin walled tube 12 are $$f_1 = \frac{r^2}{Et} \; ; f_2 = .3462 \frac{r}{Et^2} \text{ and from equation}$$

$$(3) \; W \simeq \frac{\frac{r^2}{t} \cdot p}{0.3462 \frac{r}{t^2} + 0.006079 \frac{R^3}{I}}$$

$$\text{or } W \simeq \frac{\frac{r^2}{t} \cdot h \cdot p}{.3462 \frac{rh}{t^2} + .07295(R/d)^3} \text{ by substituting } I = \frac{hd^3}{12}$$

Then from equation (2)

$$kp \simeq \frac{0.8}{\pi ET} \cdot \frac{\frac{r^2 h}{t} \cdot R^2 p}{(.3462 \frac{rh}{t^2} + .07295(R/d)^3)}$$

$$\simeq \frac{9.6}{\pi} \cdot \frac{p}{E} \cdot \frac{\frac{r}{t} \left(\frac{R}{d}\right)^2 \frac{r}{d}}{.3462 \left(\frac{r}{t}\right)^2 \frac{d}{r} \cdot \frac{h}{d} + .07295 \, (R/d)^3}$$

To reduce to a minimum allowable amount any tendency for the ring to vibrate in an "out-of-plane" mode instead of or in addition to the required "in-plane" mode the fraction $h/d$ should exceed about 5. To keep $kp$ as large as possible $r/R$ should be as large as possible, say 0.9.

$$\text{Then } kp = \frac{2.75 \frac{r}{t} p \, (R/d)^4 \times 10^{-6}}{53.85 \left(\frac{r}{t}\right)^2 + 2.0426 \, (R/d)^4}$$

Now the hoop stress in this tube under internal pressure is given by $\sigma = pr/t$, but this does not take account of the additional stress caused by the forces W. For high pressure $r/t$ must be low which means that the bending stress due to W will be low. For low pressure $r/t$ will be high as the tube should be as flexible as possible, but the bending stress will be high.

Two examples will now be worked to determine typical values of gearing factor for apparatus of FIG. 1 arranged to measure a pressure of 1000lb/in² and 10lb/in².

Pressure = 1000lb/in²

Let the hoop stress of the tube $pr/t$ = 50,000lb/in² leaving 10,000lb/in² to be attributed to bending, in this example wherein the maximum stress is half the yield stress, that is 60,000lb/in² therefore $r/t$ = 50.

If $R/d$ is of the same order as $r/t$ or higher $$kp \simeq \frac{2.75}{2.0426} \times 50,000 \times 10^{-6} \simeq .067$$

Giving a gearing factor of approximately 2(1/0.067 = 1) = 32 If $R/d$ is smaller than $r/t$, say 10

$$kp = \frac{2.75 \times 10^4 \times 10^{-6} \times 50{,}000}{53.85 \times 50^2 + 2.0426 \times 10^4} \simeq .009$$

which gives a gearing factor of 224.

$p = 10 \text{lb/in}^2$

Let the hoop stress of the tube $pr/t = 20{,}000\text{lb/in}^2$, leaving $40{,}000\text{lb/in}^2$ to be attributed to bending.

This means that $r/t$ would have to be about 2000 which is much too high for practical purposes as the wall of the tube 12 would be very thin. Reducing the value of $pr/t$ results in reducing $kp$ to unacceptably low values, e.g. if $r/t = 500$ and $R/d = 50$ this makes the two terms in the denominator about equal.

Then $kp \simeq 0.0033$ so that the gearing factor is about 608.

Thus at a relatively high pressure a gearing factor of about 32 can be obtained which is higher than the preferred maximum value of about 5 but it would be possible to construct an apparatus 10 capable of measuring the pressure of the fluid in the tube 12. However, as the change in frequency of vibration with change in pressure would be small, the resolution and accuracy of measurement would be low.

Figure 2:
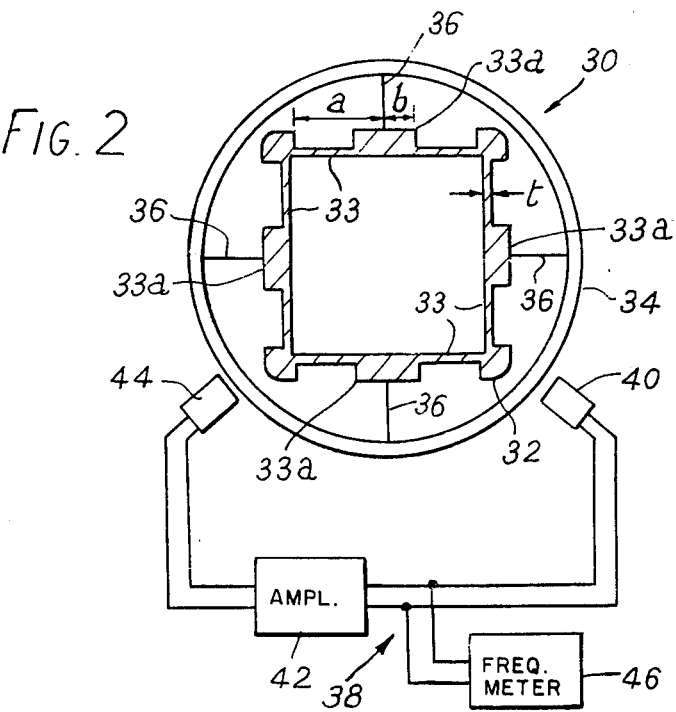
FIG. 2 is a cross-sectional view of another embodiment of apparatus according to the invention.

FIG. 2 shows a cross-sectional view of another apparatus 30 according to the invention responsive to the pressure or the pressure and the density of a fluid in a hollow body in the form of a cylindrical tube 32. The active part of the tube 32 is square and each wall of the tube has a circular piston diaphragm 33 formed therein as shown. A stiff but resilient circular ring 34 is mounted concentrically around the tube 32 by means of four struts 36 connected to the central, circular piston portion 33a of a respective diaphragm 33. The struts 36 are stiff relative to the ring 34. As described with reference to FIG. 1 the ring 34 has a rectangular cross-section, and the tube 32, ring 34 and struts 36 are made from Ni-Span-C 902.

An electromagnetic drive means 38 is provided to excite the ring 34 to vibrate continuously at its natural frequency. The drive means 38 is similar to the drive means 18 of FIG. 1 and comprises a drive coil 40, a maintaining amplifier 42, a pick-up coil 44 and a frequency meter 46 connected to operate as described with reference to FIG. 1. The drive means 38 can be so arranged that the status 36 are at points of minimum radial deflection (which can be likened to nodes) of the ring 34 when the frequency of the ring is dependent upon the pressure of fluid in the tube 32, or that the struts 36 are at points of maximum radial deflection (antinodes) of the ring when the frequency of vibration is dependent upon both the pressure and density of the fluid in the tube 32. Thus by making a first measurement the pressure of the fluid could be determined and then by making a second measurement and knowing the pressure, the density of the fluid could be derived using a single apparatus.

Expressions for the frequency of vibration of the ring 34 and $\alpha^2$ are given at equations (1) and (2) in the foregoing description with reference to FIG. 1.

As before W can be determined from a knowledge of the pressure and of the flexibilities of the ring 14 and diaphragm 33.

Let $f_1$ be the flexibility of the diaphragm 33 due to pressure of fluid.

Let $f_2$ be the flexibility of the diaphragm 33 due to force W.

Let $f_3$ be the flexibility of the ring 34 due to forces W.

Then the radial expansion of ring 34 = deflection of diaphragm 33.

$$Wf_3 = pf_1 - Wf_2$$

Hence $$W = \frac{f_1 p}{f_2} + f_3$$

It can be shown that:

$$f_1 \simeq \frac{a^4}{16D}\left[\tfrac{1}{4}(1 - (\tfrac{b}{a})^4) - (\tfrac{b}{a})^2 \log_e \tfrac{a}{b}\right] \simeq \frac{a^4 \lambda_1}{16D}$$

$$f_2 \simeq \frac{a^2}{16\pi D}\left[1 - (\tfrac{b}{a})^2 - \frac{4}{(\tfrac{a}{b})^2 - 1}\left(\log_e \tfrac{a}{b}\right)^2\right] \simeq \frac{a^2 \lambda_2}{16\pi D}$$

As described with reference to FIG. 1 $f_3 \simeq 0.006079(R^3/EI)$ where $D$ is the flexural stiffness of the diaphragm $= Et^3/12(1-v^2)$
Poisson's ratio, $v$, is taken as 0.3 in this example.

$a$ = radius of diaphragm 33
$b$ = radius of piston 33a

Substituting the values of $f_1$, $f_2$ and $f_3$ into equation 3 we obtain an expression for the force W $$W \simeq \frac{\frac{a^4 \lambda_1}{16D} p}{\frac{a^2 \lambda_2}{16\pi D} + .006079 \frac{R^3}{EI}} \tag{5}$$

which reduces to $$W \simeq \frac{.91 \times .75 \, (\tfrac{a}{t})^3 \lambda_1 p a^2}{\frac{.91 \times 75}{\pi}(\tfrac{a}{t})^3 \lambda_2 + .07295 \tfrac{a}{h}(R/d)^3}$$

therefore $\dfrac{W}{a^2} \simeq \dfrac{.6825\lambda_1 (\tfrac{a}{t})^3 p}{.21725\lambda_2 (\tfrac{a}{t})^3 + .07295 \tfrac{a}{h}(R/d)^3}$ From equation (2) an expression for $kp$ was obtained that is, $$kp \simeq \frac{.8 \times 12}{\pi E} \times \frac{WR^2}{hd^3} \simeq 1.09135 \times 10^{-7} \frac{W}{a^2}(\tfrac{R}{d})^3 \cdot \tfrac{a}{R} \, \tfrac{a}{h} \tag{6}$$

$$\simeq \frac{0.74485 \times 10^{-7} \lambda_1 (\tfrac{a}{t})^3 (R/d)^3 \tfrac{a}{R} \tfrac{a}{h} p}{.21725 \lambda_2 (\tfrac{a}{t})^3 + .07295 \tfrac{a}{n}(R/d)^3}$$

In deriving the above expression it is assumed that the stress in the diaphragms 33 is caused entirely by bending and not by any bursting effect. The maximum stress may be at the outer or inner boundary of the diaphragm 33 and it can be shown that these stresses are:

inner boundary, $$\sigma_D \simeq .375 \left(\frac{a}{t}\right)^2 \left[ 2(1 - \left(\frac{b}{a}\right)^2)p + \frac{4}{\pi} \frac{W}{a^2} \left( 1 - \frac{2a^2/b^2}{\frac{a^2}{b^2} - 1} \log_e \frac{a}{b} \right) \right]$$

outer boundary, $$\sigma_D \simeq .375 \left(\frac{a}{t}\right)^2 \left[ 2(1 - \left(\frac{b}{a}\right)^2)p - \frac{4}{\pi} \frac{W}{a^2} \left( 1 - \frac{2 \log_e \frac{a}{b}}{\frac{a^2}{b^2} - 1} \right) \right]$$

The stress in the ring 34 is given by equation 4.

$kp \simeq 3.7278 \; (R/d \cdot \sigma_R/E)$ and so the hoop stress in the ring $\sigma_R \simeq 7.511 \times 10^6 \; (kp/R/d)$ There are five geometrical parameters which may vary independently and it is necessary to determine the optimum set for a given pressure range.

There are limits for some of these parameters on practical grounds:

$a/h$ will be of the order 1

$a/R$ cannot be greater than about 0.5

$a/b$ cannot be less than 1 and should not be greater than about 5 or the strut 36 will be too large to attach to the piston portion 33a of the diaphragm 33.

Approximate values of the various parameters were determined for fluid pressures of 10, 100 and 1000 lb/in² respectively and are as follows:

$p = 10 \text{lb/in}^2$ $a/t = 100; R/d = 150; a/h = 1.0; a/R = 0.5; a/b = 5.0$ $\sigma_D = 57500 \text{lb/in}^2 \; \sigma_R = 32000 \text{lb/in}^2$ Gearing factor = 5.1

$p = 100 \text{lb/in}^2$ $a/t = 30; R/d = 60; a/n = 1.0; a/R = 0.5; a/b = 5.0$ $\sigma_D = 58000 \text{lb/in}^2 \; \sigma_R = 27000 \text{lb/in}^2$ Gearing factor 11.4
$P = 1000 \text{lb/in}^2$ $a/t = 9; R/d$ not critical; $a/h$ not critical; $a/R = 0.5; a/b = 5.0$ $\sigma_D = 58000 \text{lb/in}^2 \; \sigma_R = 6000 \text{lb/in}^2$ Gearing factor = 31.

The gearing factor is sensitive to the value of $a/t$ but insensitive to the value of $R/d$. The frequency on the other hand is extremely sensitive to $R/d$ and the choice of this parameter is governed accordingly.

Thus, although the aforementioned parameters are such that the gearing factors increase with increase in fluid pressure and at a fluid pressure of 1000 lb/in² the gearing factor would be quite high at a value of 31, it is believed that apparatus according to FIG. 2, having its parameters dimensioned as described could be used accurately to determine the pressure of a fluid in the tube 32. In a practical embodiment the frequency meter 46 could be calibrated directly in units of pressure according to the pressure range of the apparatus 30.

To determine density, the drive means 38 is so arranged that the ring 34 vibrates with the struts 36 at the antinodes whereby the piston diaphragms 33 are driven as well. This causes fluid to be pumped backwards and forwards between adjacent pistion 33a.

The frequency of vibration of the ring 32 and diaphragms 33 combined can be shown to be:

$$f = \frac{1}{2\pi} \sqrt{ \frac{\frac{3}{4} \frac{Eg}{\gamma R^2} \left(\frac{d}{R}\right)^2 \left[ 1 + \frac{2}{9} \frac{\pi^2}{(.91)} \frac{\left(\frac{R}{d}\right)^3 \left(\frac{t}{a}\right)^3 \frac{a}{h}}{\left(1 - \frac{b}{a}\right)^2} - \frac{\pi^2}{4} \frac{\left(\left(\frac{a}{b}\right)^2 - 1\right)}{\left(\frac{a}{b} - 1\right)^2} + C + \frac{1}{2} \log_e \frac{a}{b} \right) + \frac{112}{15\pi E} \frac{W}{a^2} \left(\frac{R}{d}\right)^3 \frac{a}{R} \frac{a}{h} \right]}{\frac{5}{4} + \left(\frac{a}{R}\right)^2 \frac{a}{h} \frac{R}{d} \frac{t}{a} \left[ \frac{3}{2} \left(1 - \left(\frac{b}{a}\right)^2\right) - \frac{8}{\pi^2} \left(1 - \left(\frac{b}{a}\right)^2\right) + 4 \frac{C}{t} \left(\frac{b}{a}\right)^2 \right] } } \quad (7)$$

where $C = \int_b^a \frac{1}{r} \cos 2n\pi \left(\frac{r - b}{a - b}\right) dr$

This does not include the effect of inertia of the fluid.

As before this may be expressed as $f' \simeq f_0' \; a'$, the frequency of the ring and diaphragms, vibrating together, with zero pressure times a factor dependent upon the pressure.

-continued $$\text{where } \alpha'^2 \simeq \frac{1 + \frac{112}{15\pi i E} \frac{W}{a^2} \left(\frac{R}{d}\right)^3 \frac{a}{R} \frac{a}{h} \left(1 - \frac{b}{a}\right)^2}{1 + \frac{2}{9} \frac{\pi^2}{(.91)} \left(\frac{R}{d}\right)^3 \left(\frac{t}{a}\right)^3 \frac{a}{h} \left[\frac{\pi^2}{4} \frac{\left(\left(\frac{a}{b}\right)^2 - 1\right)}{\left(\frac{a}{b} - 1\right)^2} + C + \frac{1}{2} \log_e \frac{a}{b}\right]}$$

Clearly $k'p$ is less than $kp$ but this is not a disadvantage in this case because the density of the fluid is to be determined and the less sensitive the frequency is to pressure the better.

To include the effect of the inertia of the fluid some assumption must be made about the quantity and region of fluid involved in the pumping action. It has been assumed that the fluid flows backwards and forwards around a circular arc of radius $a$ having its origin at the junction of two diaphragms and cross-sectional area half that of the piston portion 33a.

Each quadrant of fluid has a weight of $(\pi b^2/2) \times (\pi a/2) \cdot \Omega$ where $\Omega$ is the specific weight of the fluid in lb/in³. This weight my be added to that of each piston 33a to find the effect of it upon the frequency. The term $$\pi \cdot \frac{b^2}{a} \cdot \frac{a^2}{R} \cdot \frac{a}{h} \cdot \frac{R}{d} \cdot \frac{\Omega}{\gamma}$$

may then be added to the denominator of the expression for frequency at equation (7). It should be noted however that $$\frac{\Omega}{a} = \frac{\Omega}{a} \times \frac{aw}{aw} = \frac{\Omega}{aw} \times \frac{aw}{a}$$

where $\gamma w$ is the specific weight of water and so $\Omega/\gamma w$ is the specific gravity of the fluid and $\gamma/\gamma w$ is the specific gravity of the material, in this case Ni-Span-C 902. The specific gravity of Ni-Span-C 902 is 8.15. The frequency equation may be rewritten:

$$f = (fo'/\beta) \alpha'$$

$\beta$ being an inverse factor on the natural frequency dependent upon the specific gravity of the fluid, $\alpha'$ is a factor dependent upon the pressure where $\beta^2 \simeq 1 + q\eta$ and $\eta = \Omega/\gamma w$ specific gravity of fluid.

$$\text{and } \phi \eta \simeq \frac{\frac{\pi}{8.15} \left(\frac{b}{a}\right)^2 \left(\frac{a}{R}\right)^2 \frac{a}{h} \frac{R}{d} \eta}{\frac{5}{4} + \left(\frac{a}{R}\right)^2 \frac{a}{h} \frac{R}{d} \frac{t}{a} \left[\frac{3}{2}\left(1 - \left(\frac{b}{a}\right)^2\right) - \frac{8}{\pi^2}\left(1 - \frac{b}{a}\right)^2 + 4\frac{c}{t}\left(\frac{b}{a}\right)^2\right]}$$

$$= \frac{\text{Equivalent mass of vibrating fluid}}{\text{Equivalent mass of piston and diaphragm}}$$

The parameter $c/t$ should be between 5 and 10 and the term which includes it predominates therefore.

$$\text{therefore } q\,\eta \simeq \frac{\pi}{8.15 \times 4} \cdot \frac{a}{c} \cdot \eta$$

If $c/t = 10$ and $a/t = 100$ as is recommended for the apparatus when designed to determine pressures of the order of 10 lb/in².

$$q\eta \frac{10}{32.6} \eta = .307\eta$$

For a liquid of specific gravity $= 1$, $q\eta = 0.307$ and the gearing factor $= +2(1 + 1/q\eta) = -8.5$.

For the higher pressures:

$p = 100$ lb/in²
$a/t = 30$, if $c/t = 5$ therefore $q\eta = 6/32.6\,\eta = 0.184\,\eta$ and for $\eta = 1$ the gearing factor $= -13$.
$p = 1000$ lb/in²
$a/t = 9$, if $c/t = 5$
$q\eta = (9/5)/32.6 = 0.055$ and for $\eta = 1$ the gearing factor $= -38$.

thus at low fluid pressures, the gearing factor for density determination, although not as low as for pressure determination is low enough to enable reasonably accurate determination of the density of the fluid. At fluid pressures of about 100 lb/in² the gearing factor is quite high but may be acceptable for the secondary determination of density. At higher pressures, such as about 1000 lb/in², the gearing factor is probably too high for accurate density determination in relation to the accuracy obtainable for the pressure of the fluid.

Figure 3:
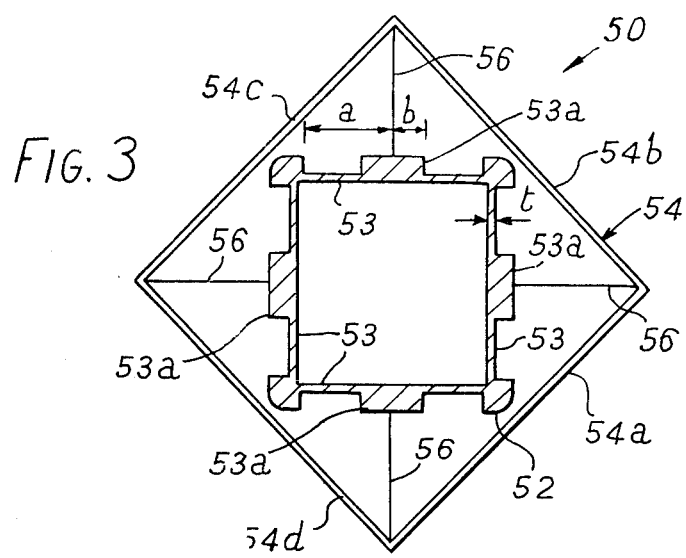
FIG. 3 is a cross-sectional view of a third embodiment of apparatus according to the invention.

FIG. 3 shows a third embodiment of apparatus 50 according to the invention which is responsive to the pressure of fluid in a tube 52. The tube 52 is similar to the tube 32 of FIG. 2. A ring 54 comprising four substantially identical stiff but resilient, rectilinear limbs 54a - d is mounted concentrically with the tube by means of four struts 56 which are connected to and extend between an associated piston portion 53a of a diaphragm and the junction of two limbs 54 as shown. The tube 52, ring 54 and structs 56 are of Ni-Span-C 902. Electromagnetic drive means (not shown) which may be as described with reference to FIGS. 1 and 2 is provided to cause the limbs to vibrate continuously at their common natural frequency. The limbs are arranged to vibrate in such a manner that while two opposed limbs are deflecting outwardly, the other two opposed limbs are deflecting inwardly. Thus it will be realized that the limbs vibrate in a manner similar to four simple beams in contradistinction to the circular rings of FIGS. 1 and 2 which vibrate in a hoop made.

A square ring under four equal outwardly directed diagonal forces is not subjected to bending at all, only to tension, and is in consequence much stiffer than a circular ring of similar proportions.

There are, however, some further differences between the square ring 54 and the circular rings 14 and 34; the vibrations of the latter are inextensional in that their circumference does not change in the course of a cycle of vibration. This allows the struts to be connected to the ring at radial nodes and the diaphragms remain stationary. When the square ring 54 vibrates with in-plane bending the linear distance between the corners is reduced by the flexure and the corners move inwardly driving the diaphragms 53 at twice the frequency of the ring 54.

In deriving an approximate expression for the frequency of vibration of the ring 54 certain assumptions may be made:

i. if the length of a limb is L and its amplitude of vibration is $a_1$, the ratio of the amplitude of vibration $a_1$ to the length L, will be very much less than unity and typically would be about 1/1000 or less.

ii. the ratio $a/t$ of the radius $a$ of the diaphragm 53 to the thickness $t$ of the diaphragm is approximately equal to the ratio $L/d$ of the length L of the limb 54 to the thickness $d$ of the cross-section of the limb.

iii. the ratio $a/h$ of the radius $a$ of the diaphragm to the width h of the cross-section of the diaphragm is about 4.

iv. the flexibility $f_3$ of the ring due to the force W in the struts caused by pressure $p$ is very much less than the flexibility $f_2$ of the diaphragm due to the force W.

By making the above assumptions it can be shown that the frequency $f$ of the ring in vibration can be obtained from the expression:

$$f^2 = f_o^2 \alpha^2$$

$$f^2 \simeq \frac{1}{4\pi^2} \frac{EI\pi^4}{mL^4} \left[1 + \frac{L^2}{\sqrt{2}\ \pi^2 EI} \frac{f_1}{f_2+f_3} p\right) 1 + \frac{\pi}{2} \frac{f_2}{f_1} \left[a^2 - \frac{4}{\pi^2}(a-b)^2\right]\right]$$

$$\alpha^2 \simeq 1 + \frac{L^2}{\sqrt{2}\ \pi^2 EI} \frac{f_1}{(f_2+f_3)} p \left[1 + \frac{\pi}{2} \frac{f_2}{f_1}\left(a^2 - \frac{4}{\pi^2}(a-b)^2\right)\right]$$

therefore $$f^2 \simeq f_o^2 [1 + k_o p Q] = f_o^2 [1 + kp$$

where $k_o p$ is a value ignoring the coupling effect between the ring and the diaphragm.

$$k_o p \simeq \frac{L^2}{\sqrt{2}\ \pi^2 EI} \cdot \frac{F_1 p}{F_1 + f_3}$$

Q is a further amplification factor caused by net work being done by the diaphragms on the internal pressure due to the fluid, over a cycle, thus increasing the level of initial tension in the ring 54, and $$Q \simeq 1 + \frac{\pi}{2} \frac{f_2}{f_1}(a^2 - \frac{4}{\pi^2}(a-b)^2).$$

From the description with respect to FIG. 2 it will be seen $$\frac{f_2}{f_1} = \frac{1}{a^2\pi} \frac{\lambda_2}{\lambda_1}.$$

Therefore $$Q \simeq 1 + \frac{1}{2}(1 - \frac{4}{\pi^2}(1 - \frac{b}{a})^2)\frac{\lambda_2}{\lambda_1}$$

which is always greater than unity because the ratio $b/a$ is less than 1.

If the ratio $a/b = 1.5$, $Q = 2.38$
If the ratio $a/b = 2.0$, $Q = 2.61$

A considerable effect which is quite fortuitous. By substituting for the values of I, $f_1$, $f_2$ and $f_3$ $$kp = \frac{\frac{12}{\sqrt{2}\ \pi^2} \frac{p}{E} (\frac{a}{t})^3 (\frac{L}{d})^3 (\frac{a}{L}) (\frac{a}{h}) \frac{\lambda_1}{16D} Q}{\frac{\lambda_2}{16\pi D}(\frac{a}{t})^3 + \frac{1}{2}\frac{a}{h}\frac{L}{d}}$$

If the value of Young's modulus E, for Ni-Span-C 902 is $28 \times 10^6$ lb/in$^2$ then $$kp \simeq \frac{2.0956 \times 10^{-8}(\frac{a}{t})^3(\frac{L}{d})^3(\frac{a}{L})\ (\frac{a}{h})\lambda_1 Q p}{.21725\lambda_2(\frac{a}{t})^3 + 0.5(\frac{a}{h})\ (\frac{L}{d})}$$

for $\frac{a}{b} = 1.5 \lambda_2 = .029$, $\frac{\lambda_1}{\lambda_2} Q = 1.648$ If ratios $a/h = 4$ and $L/d = a/t = 50$ say, then although the said term in the denominator is not negligible in comparison with the first, a value for $kp$ can be obtained within 10 percent if the second term is ignored.

On doing this the parameter $a/t$ disappears from the expression giving (9)

$$kp \simeq \frac{12}{\sqrt{2}\ \pi} \frac{p}{E} \left(\frac{\lambda_1}{\lambda_2} Q\right)(\frac{L}{d})^3 (\frac{a}{L}) (\frac{a}{h})$$

The ratio $a/L$ should not be greater than about 0.25, otherwise the ring 54 will be too small to go around the tube 52.

By inspection of the expression for $kp$ it will be seen that:

i. the ratio $a/h$ should be as large as possible but if it is too large the thickness $d$ of the ring 54 will exceed the width $h$ and the cross-sectional dimensions of the ring will be small. A value of four appears to be a reasonable compromise for the ratio $a/h$.

If the length L of each limb 54 is made equal to 4 inches them, from the foregoing, the radius $a$ of the diaphragm 53 should be 0.25 L which is 1 inch and the width h of the ring should be $a/4$ which is 0.25 inches.

If the thickness $d$ of each limb $54a$ to $d$ is 0.05 inches and Yound's Modulus E is $28 \times 10^6$ lb/in$^2$, then from equation (9)

$$kp = 9.646 \times 10^{-8} \left(\frac{\lambda_1}{\lambda_2} \cdot Q\right)\left(\frac{L}{d}\right)\left(\frac{a}{L}\right)\left(\frac{a}{h}\right) \cdot p$$

and with the parameter values above $$kp = 0.04939 \, p$$

As aforementioned with reference to FIGS. 1 and 2 the gearing factor = $2(1+1/kp)$ For a fluid pressure $p = -15$ psi e.g. vacuum inside the tube 52 and the ring in compression, the gearing factor $\simeq -0.7$ which is very sensitive. For a fluid pressure, $p = +15$ psi, the gearing factor = 4.7. The gearing factor of the apparatus as descrbed for different pressure differences across the wall of the tube 52 may be tabulated as follows:

| Pressure difference psi | −15 | −10 | −5 | +5 | +10 | +15 | +20 |
|---|---|---|---|---|---|---|---|
| Gearing factor | −0.7 | −2.1 | −6.1 | +10 | +6.1 | +4.7 | +4.0 |

Furthermore the gearing factor appears to be satisfactory over a wide range of pressures.

The stresses in both ring 54 and diaphragm 53 are much less than in the corresponding components of the other two arrangements.

Thus various embodiments of apparatus responsive to pressure have been described, some of which can also be made responsive to the pressure and density of a fluid thereby allowing both pressure and density to be determined from a single apparatus, or pressure transducer.

Figure 4:
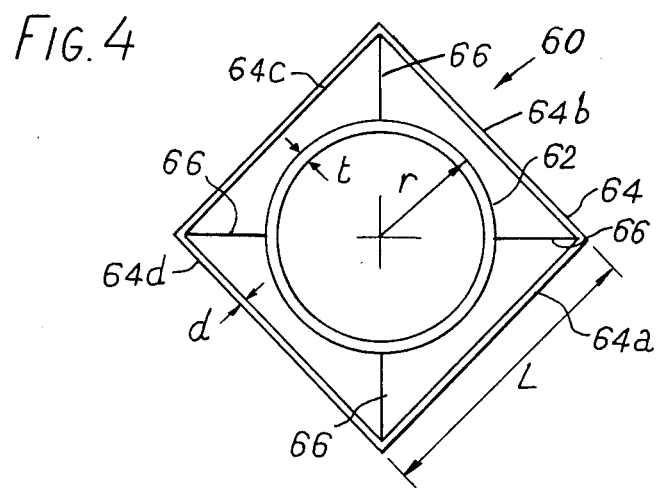
FIG. 4 is a cross-sectional view of a fourth embodiment of apparatus according to the invention.

FIG. 4 shows a fourth embodiment of apparatus 60 according to the invention which is responsive to the pressure of fluid in a tube 62. The tube 62 is similar to the tube 12 of FIG. 1. A ring 64 comprising four substantially identical stiff but resilient, rectilinear limbs $64a - d$ is mounted concentrically with the tube 62 by means of four struts 66 in a manner similar to that described with reference to FIG. 3. The tube 62, ring 64 and struts 66 are of Ni-Span-C 902. Electromagnetic means (not shown) which may be as described with reference to FIGS. 1 and 2 is provided to cause the limbs $64a - d$ to vibrate continuously at their natural frequency in a manner similar to that described with reference to FIG. 3.

Again, the frequency of vibration can be expressed in the form:

$$f = f_o \alpha$$

where $f_o$ is the frequency with zero pressure $\alpha$ is the amplification factor caused by pressure.

$$f_o = \sqrt{\frac{EI \cdot \pi^2}{4mL^4}} \quad m = \text{mass per unit length of ring} = \text{total mass}/4L$$

and $\alpha^2 = 1 + kp = \frac{12}{\sqrt{2} \pi^2} \cdot \frac{\frac{r}{d}\left(\frac{L}{d}\right)^2 \frac{r}{t} \frac{p}{E}}{.3462 \frac{h}{d} \frac{d}{r}\left(\frac{r}{t}\right)^2 + \frac{1}{4}\frac{L}{d}} + 1$ For a pressure of 1000 lb/in$^2$ and with stresses not exceeding 10,000 lb/in$^2$ (which ignores the bending stress in the tube caused by the struts) a satisfactory gearing factor can be achieved.

Using $L/d = 50; r/t = 10; r/d = 20$ and $h/d = 5$ values which keep the stresses below the stated level and do not violate any geometrical constraints, $kp = 0.425$ and Gearing Factor = 6.7.

Other transducers according to the invention are, of course, possible and the described transducers can be subject to modifications. For example the transducer could be enclosed and the space between the tube and the enclosure could be supplied with a fluid at a higher pressure than that supplied to the tube. Under these conditions the ring would be in compression and it is believed that the transducer may be more sensitive to changes in pressure.

Figure 5:
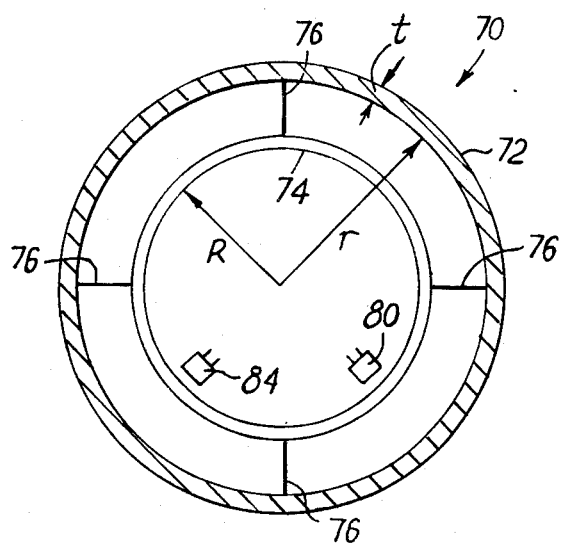
FIG. 5 is a cross-sectional view of a fifth embodiment of apparatus according to the invention.

In another arrangement the ring could be mounted within the tube, for use for example as an insertion transducer whereby the transducer acts as a probe. As illustrated in FIG. 5, such an embodiment might include an Apparatus 70 having a tube 72 connected through struts 76 to support a ring 74 within the tube 72. As in previous embodiments, a drive coil 80 and a pick-up coil 84 can be provided to produce an electrical output signal representative of the frequency of vibration.

An arrangement in which the square ring 54 is mounted upon the tube 12 is also viable and can be shown to give acceptable gearing factors for pressure differences of the order of 1000 lb/in$^2$.

Ni-Span C 902 is made by: Huntington Alloy Products Division, The International Nickel Company, Inc. Huntington W.V., and in Bulletin T31 entitled "Engineering properties of Ni-Span-C iron nickel-chromium alloy 902" it is stated to have the following constituents:

| Nickel (plus cobalt) | 41.0 | to | 43.50 |
|---|---|---|---|
| Chromium | 4.90 | to | 5.75 |
| Titanium | 2.20 | to | 2.75 |
| Aluminium | 0.30 | to | 0.80 |
| Carbon | 0.06 | max. | |
| Manganese | 0.80 | max. | |
| Silicon | 1.00 | max. | |
| Sulphur | 0.04 | max. | |
| Phosphorus | 0.04 | | |
| Iron | | remainder | |

I claim:

1. Apparatus responsive to the pressure of a fluid contained in or surrounding a stiff but resilient hollow body, comprising a stiff but resilient ring, $2n$ (where $n$ is an integer greater than 1) equi-spaced radially extending struts connected between a periphery of said ring and a peripheral surface of said body to support said ring concentrically with said body, means for exciting natural vibrations of said ring at a resonance frequency and means for providing a signal representative of the frequency of said vibrations.

2. Apparatus according to claim 1, in which the hollow body has a cylindrical wall member concentric with the ring.

3. Apparatus according to claim 2, in which the hollow body is provided with $2n$ piston diagraphms in the wall thereof, wherein opposed diaphragms are arranged substantially parallel to each other, and an end of each strut is connected to the centre of an associated diaphragm.

4. Apparatus according to claim 1, in which the ring is cylindrical and of circular cross-section.

5. Apparatus according to claim 1, in which the ring is circular and of oblong cross-section with its minor axis extending in the radial direction.

6. Apparatus according to claim 5, in which the ring is of rectangular cross-section.

7. Apparatus according to claim 3, in which the ring is cylindrical and of circular cross-section.

8. Apparatus according to claim 3, in which the ring is circular and of oblong cross-section with its minor axis extending in the radial direction.

9. Apparatus according to claim 8, in which the ring is of rectangular cross-section.

10. Apparatus according to claim 1, in which said means for exciting natural vibrations in said ring is so arranged that points of minimum radial deflection of said ring occur at the points of connection to said struts.

11. Apparatus according to claim 10 in which said means for exciting natural vibrations in said ring is selectively arranged to cause the points of maximum radial deflection of said ring to occur at the points of connection to the struts, whereby the frequency of said vibrations is dependent upon the pressure and the density of the fluid under investigation.

12. Apparatus according to claim 3, in which said means for exciting natural vibrations in said ring is so arranged that points of minimum radial deflection of said ring occur at the points of connection to said struts.

13. Apparatus according to claim 12 in which said means for exciting natural vibrations in said ring is selectively arranged to cause the points of maximum radial deflection of said ring to occur at the points of connection to the struts, whereby the frequency of said vibrations is dependent upon the pressure and the density of the fluid under investigation.

14. Apparatus according to claim 1, in which the ring comprises $2n$ rectilinear, stiff but resilient limbs and said struts are connected to the junctions thereof.

15. Apparatus according to claim 14 in which $n = 2$ and the ring is in the form of a square.

16. Apparatus according to claim 1 in which said ring is outside said body.

17. Apparatus according to claim 16 in which said fluid is supplied to the inside of said body.

18. Apparatus according to claim 3 in which said ring is outside said body.

19. Apparatus according to claim 18 in which said fluid is supplied to the inside of said body.

20. Apparatus according to claim 15 in which said ring is outside said body.

21. Apparatus according to claim 20 in which said fluid is supplied to the inside of said body.

22. Apparatus according to claim 1, in which said ring is mounted within said body.

23. Apparatus according to claim 1, enclosed in a housing having means for supplying, in use, the space between said body and said housing with a fluid at a higher pressure than that supplied internally of said body.

24. Apparatus according to claim 3, enclosed in a housing having means for supplying, in use, the space between said tube and said housing with a fluid at a higher pressure than that supplied internally of said body.

25. Apparatus according to claim 1, in which said ring, body and struts are made of a ferromagnetic metal, such as Ni-Span C 902.

26. Apparatus according to claim 3, in which said ring, body and struts are made of a ferromagnetic metal, such as Ni-Span C 902.

27. Apparatus according to claim 14, in which said ring, body and struts are made of a ferromagnetic metal, such as Ni-Span C 902.

* * * * *

UNITED STATES PATENT OFFICE
CERTIFICATE OF CORRECTION

Patent No. 4,048,846  Dated Sept. 20, 1977

Inventor(s) Reginald Catherall

It is certified that error appears in the above-identified patent and that said Letters Patent are hereby corrected as shown below:

| | |
|---|---|
| Column 2, line 12 | after "Young's", insert --Modulus-- |
| Column 4, line 24 | that portion of the equation which reads "$\frac{rn}{t^2}$" should read -- $\frac{rh}{t^2}$ -- |
| line 67 | delete " = ", insert -- + -- |
| Column 5, line 47 | "status" should read --struts-- |
| Column 6, line 14 | "$W = \frac{f_2 p}{f_2} + f_3$" should read -- $W = \frac{f_1 p}{f_2} + f_3$ -- |
| Column 8, line 17 | "D" should read -- $\sigma_D$ -- |
| line 17 | "R" should read -- $\sigma_R$ -- |
| Columns 9 & 10 lines 1 thru 10 | complete the equation by adding -- $= 1 + k'p$ -- |
| Column 9 lines 36 & 37 | "$\frac{\Omega}{\alpha} = \frac{\Omega}{\alpha'} \times \frac{\alpha w}{\alpha w} = \frac{\Omega}{\alpha w} \times \frac{\alpha w}{\alpha}$" should read -- $\frac{\Omega}{\gamma} = \frac{\Omega}{\gamma} \times \frac{\gamma_w}{\gamma_w} = \frac{\Omega}{\gamma_w} \times \frac{\gamma_w}{\gamma}$ -- |
| lines 39, 40 & 49 | in four instances "$\gamma w$" should read -- $\gamma_w$ -- |
| line 44 | "$f = (fo'/\beta) \alpha'$" should read -- $f' = (fo'/\beta) \alpha'$ -- |
| line 55 | "and $\phi \eta \simeq$" should read -- and $q \eta \simeq$ -- |
| line 61 | delete "therefore." |

UNITED STATES PATENT OFFICE
CERTIFICATE OF CORRECTION

Patent No. 4,048,846        Dated Sept. 20, 1977

Inventor(s) Reginald Catherall

It is certified that error appears in the above-identified patent and that said Letters Patent are hereby corrected as shown below:

Column 10, line 17     " = +2" should read -- = -2 -- line 68     "made" should be --mode--

Column 11, line 40     in the first instance " ) " should be -- ( -- line 50     after "[1 + kp" insert -- ] --

Column 12, line 66     "them" should read --then--

Column 13, line 2     "Yound's" should read --Young's--

Signed and Sealed this

Sixth Day of February 1979

[SEAL]

Attest:

RUTH C. MASON
*Attesting Officer*

DONALD W. BANNER
*Commissioner of Patents and Trademarks*